United States Patent [19]

Gagnieu et al.

[11] Patent Number: 5,763,579
[45] Date of Patent: Jun. 9, 1998

[54] COLLAGEN DERIVATIVES, PROCESS FOR PRODUCING THEM AND THEIR APPLICATION TO THE PREPARATION OF BIOMATERIALS

[75] Inventors: Christian Gagnieu, Chassieu; Florence Nicolas, Villeurbanne; Gérard Soula, Meyzieu, all of France

[73] Assignee: Flamel Technologies, Venissieux Cedex, France

[21] Appl. No.: 454,189

[22] PCT Filed: Dec. 16, 1993

[86] PCT No.: PCT/FR93/01258

§ 371 Date: Jun. 16, 1995

§ 102(e) Date: Jun. 16, 1995

[87] PCT Pub. No.: WO94/13731

PCT Pub. Date: Jun. 23, 1994

[30] Foreign Application Priority Data

Dec. 16, 1992 [FR] France ................... 92 15429

[51] Int. Cl.$^6$ .............. A61K 38/17; A61K 9/70; C07K 13/00
[52] U.S. Cl. .............. 530/356; 530/402; 530/408; 530/410; 424/443; 424/444; 424/445; 424/484; 602/42; 602/43; 602/48; 602/50
[58] Field of Search .............. 530/356, 402, 530/408, 410; 424/443, 444, 445, 484; 602/42, 43, 48, 50

[56] References Cited

U.S. PATENT DOCUMENTS

| | | | |
|---|---|---|---|
| 3,111,512 | 11/1963 | Benesch et al. | 530/356 |
| 4,294,241 | 10/1981 | Miyata | 128/156 |
| 4,407,787 | 10/1983 | Steinberger | 424/28 |
| 5,219,895 | 6/1993 | Kelman et al. | 522/68 |
| 5,412,076 | 5/1995 | Gagnieu | 530/356 |

*Primary Examiner*—Cecilia J. Tsang
*Assistant Examiner*—Abdel A. Mohamed
*Attorney, Agent, or Firm*—Bacon & Thomas

[57] ABSTRACT

The present invention relates to a modified collagen which is soluble in water and/or in aprotic polar organic solvents and which comprises free or substituted thiol functional groups carried by residues of cysteine or its derivatives, the residues being, at least partially, residues which are directly grafted onto the collagen chain, characterized in that it possesses a level of free or substituted thiol functional groups greater than 0.3, preferably 0.5 mM/g of collagen. The invention also relates to the production of these new collagen derivatives and to their application in the preparation of biomaterials, it being possible for the latter to be used especially in the manufacture of implants, prostheses or the like.

30 Claims, No Drawings

COLLAGEN DERIVATIVES, PROCESS FOR PRODUCING THEM AND THEIR APPLICATION TO THE PREPARATION OF BIOMATERIALS

TECHNICAL FIELD

The present invention relates to new collagen derivatives, in particular which can be cross-linked and which are capable of being used, especially in the preparation of biomaterials, from which products, which are applicable especially in medicine and more particularly in surgery or cosmetics, can be obtained.

Among these products, there may be mentioned artificial tissues or organs such as artificial skin, bone, ligament, cardiovascular or intraocular prostheses or implants and the like, or alternatively bioencapsulation systems (implants, microspheres and microcapsules) which permit the controlled release of active ingredients in vivo.

As example, there may also be mentioned medical accessories such as suture threads or coatings for the biocompatibilization of implantable medical items.

The invention also relates to processes for producing these new collagen derivatives as well as new intermediate products which are involved in the abovementioned process and, finally, the cross-linked collagen derived from the cross-linkable collagen which is among the new collagen derivatives conforming to the invention.

The field of the invention is that of biocompatible materials based on collagen, which are useful as raw material for the production of items intended to be placed in contact with or implanted in the human or animal body and which are capable of becoming perfectly assimilated into the biological materials, especially from the mechanical point of view, so as to be able to replace them.

Collagen is a known protein which is present at all levels of the organization of the connective tissues: it is the principle protein of the skin and the connective tissue. By nature, it has biochemical and physico-chemical characteristics which are relatively quite suitable for uses as biomaterials.

For the purposes of the resent invention, the term collagen designates any peptide of collagenic nature, such as collagen, denatured collagen and gelatin.

PRIOR ART

Various qualities of collagen of animal or human origin are currently marketed world-wide, essentially for the elaboration of biomaterials or cosmetic products.

In the applications which are currently widespread, the properties of the various qualities available are sufficient.

Thus, among these collagens, there are excellent supports for cell adhesion, multiplication and growth, which are valued for the production of cell culture media.

Advantage is also taken of their hydrophilicity, their low immunogenicity, their high resistance to proteolysis and their hemostatic character.

The mechanical properties of native collagens are acceptable for a number of uses.

Nevertheless, it has to be recognized that, in the field of implantable medical items such as implants and prostheses, the native collagens on the market suffer major defects with respect to their mechanical resistance and their resistance to proteolysis.

Indeed, the introduction of these foreign bodies, which implants and prostheses represent, into a living organism induces rejection phenomena which result especially in inflammatory reactions causing, inter alia, the production of collagenase, which hydrolyzes collagen. This results, at the very least, in an alteration of the mechanical behavior of the collagen-based transplant.

It is known that cross-linking makes it possible to improve the mechanical properties of collagen. It confers a very high tensile strength, tear strength and resistance to enzymatic degradation on the collagen fibers by virtue of the numerous covalent bonds which it creates between the collagen chains.

On the basis of this scientific knowledge, numerous studies have been undertaken in order to develop the possibilities of artificial cross-linking of collagen.

Three main types of techniques for cross-linking this protein thus emerged.

The first type of technique is cross-linking by means of a bridging agent in which the exogenous molecules, which are most often bifunctional, react in order to allow the formation of bonds. The reagents most frequently used are:

Mono- and dialdehydes, such as formaldehyde (which generates methylene bridges), malonaldehyde and, especially, glutaraldehyde (which cross-links via imine and aldol bonds). The main problems are due to their —CHO ends which are irritant and to the self polymerization of the dialdehydes which produces cytotoxic polymers.

Dicarboxylic compounds. They are, to date, essentially used either to modify collagen or for tanning skins. They react via formation of amide or even ester bonds.

Diamines such as hexamethylene diamine, which act only via amide bonds.

Diisocyanates, including hexamethylene diisocyanate which is used for cross-linking via amide bonds.

Disulfonyl chlorides which form intra- and inter-chain bonds.

According to a second type of technique, a network is created via covalent bonding between the collagen molecules, and this without grafting exogenous compounds.

The principle methods used are:

Irradiation (ultraviolet or gamma radiation) which produces both a number of oxidative deaminations permitting cross-linkages via imine and aldol bonds, as well as highly reactive free radicals capable of creating covalent bridges. Such a method has the disadvantage of causing the cross-linking of collagen only in a narrow low-energy range. For higher energy values, it brings about hydrolyses or denaturations which are very damaging to the product.

Extensive dehydration (more than 100° C. under vacuum) which results in the formation of amide and ester bonds, as well as intra- and intermolecular lysino-alanines. Among the reagents used, there may be mentioned carbodiimides such as cyanamide or dicyclo-hexylcarbodiimide. This method of cross-linking is still at the experimental stage.

Enzymatic cross-linking via proteins mimicking the effect of lysyloxidase (enzyme responsible for the natural cross-linking). This is, for the moment, still being studied.

Oxidation-reduction which induces an oxidative deamination of the amine-containing ends which become aldehydic. Metallic cations ($Cu^{2+}$, $Fe^{2+}$, $Al^{3+}$) combined with cofactors (ascorbate, pyridoxal-5P), as well as sulfites or nitrites, are essentially used. This method is very useful for the tanning of leather.

Functional activation, in particular of the carboxyls which can provide acid azides having a very selective reactivity with respect to the —NH$_2$ ends and resulting in the formation of an amide bond. Various biomaterials can thus be produced.

The third type of technique is copolymerization cross-linking.

It consists in combining, via covalent bonds, collagen with another polymer to give more or less interlaced conformations. The polymers most often associated with collagen are:

Acrylic derivatives whose toxicity often rules out its use in implant type applications in human medicine.

Acrylonitrile-styrene mixtures with which it has up until now not been possible to go beyond the laboratory stage.

Polyurethanes which are especially used in strengthening tanned leathers.

Polyalcohols.

Silicones.

The bonds involved in copolymerization are wide ranging and depend on the groups presented by each polymer.

All these techniques, whether of physical or chemical nature, possess numerous disadvantages.

Firstly, in the case of chemical cross-linkages, they give rise to toxic residues in the cross-linked collagen. The residues can be in the form of reagents which are not used up, or free reactive functional groups derived from bifunctional reagents which have reacted via only one end.

Generally, these two types of cross-linking cause a partial or total loss of the affinity of tissue cells for modified collagen.

In addition, they cannot be used for producing molded items from collagen solutions. Indeed, none of them makes it possible to control the kinetics of cross-linking, or the level of cross-linking.

Under such unpredictable conditions, it is not possible to envisage industrial manufacturing processes which are simple, economical and resulting in products with a mechanical quality which is adapted to the intended applications.

That is why, in the great majority of cases, cross-linking techniques have been used in a limitative manner on anatomical components or on tissues containing collagen.

More exceptionally, they are used for the cross-linking of preformed collagen items, essentially films or felts.

In any case, they remain ineffective in the remaining wide field of applications as biomaterials.

Furthermore, it has been proposed to exploit the bridge most commonly encountered from the biological point of view, the —S—S— disulfide bond.

The article entitled "Einbau von cystin-brücken in kollagen", F. SCHADE & H. ZAHN, Angew. Chem 74, 904 (1962), thus describes the direct attachment of a cystine derivative to collagen, in order to try to perform cross-linking via —S—S— bridge.

In this brief summary of their work, the authors claim to have obtained cross-linked collagen via disulfide bridges.

The cross-linking agent used is a cystine derivative in which the two amine functional groups of the cystine were blocked with a protecting group of the benzyloxycarbonyl type and in which the two acid functional groups of the cystine were activated by esterification by means of nitrophenol.

The grafting of this cystine derivative onto collagen is performed in a neutral medium based on dimethyl formamide and water.

After grafting onto collagen, the disulfide bridges were reduced, then reoxidized by atmospheric oxygen (self-cross-linking factor) in basic medium.

Even under theoretical optimal conditions, the direct grafting technique used makes it possible to achieve only low levels of substitution, equal to a maximum of 0.3 mM/g of collagen, which corresponds to the grafting of a free or substituted thiol functional group on each lysyl residue in the collagen.

Throughout the present account, the level of grafting upon collagen is expressed in millimoles of free or substituted thiol functional groups per gram of collagen (mM/g).

Twenty years after this first article, Patent Application EP 0.049.469 discloses a dressing based on collagen and fibrinogen-forming agent combined. In this document, the direct introduction of thiol functional groups into soluble collagen extracted from tendons is described. The thiol functional groups are provided via N-acetylhomocysteine thiolactone.

In the same manner as above, the grafting of this molecule onto collagen can occur only on the free amine-containing radicals carried by the lysyl residues, which is equivalent to a maximum grafting level of 0.3 mM/g, assuming that the reaction is complete.

This is corroborated by an article by BENESCH & BENESCH, "Proceeding of the National Academy of USA", vol. 44, 1958, p. 848–853, in which Table I of page 849 shows that the maximum grafting level, in SH functional groups, obtained is 0.295 mM/g, and this even in the presence of large excess amounts of thiolactone.

It therefore has to be said that these two earlier techniques use collagens onto which cysteic residues are directly grafted and thus offer, theoretically, the possibility of carrying out cross-linkages via S—S bridges. But these earlier techniques have the major disadvantage of imposing a limitation with respect to the number of S—S bridges which can be envisaged, which rules out their use.

They did not therefore lead to concrete bio-medical applications.

Consequently, under these circumstances, the present invention aims to provide a modified collagen which is soluble in water and/or in aprotic polar organic solvents and which carries free or substituted thiol functional groups belonging to residues of cysteine or its derivatives. Another aim of the invention is to provide a modified collagen which is cross-linkable, that is to say capable of being cross-linked by formation of disulfide bridges in the presence of mild oxidants, by permitting an excellent control of the kinetics and level of cross-linking.

Another aim of the invention is to provide a "thiolized" collagen which is cross-linkable into gels with cross-linking density, and therefore with a mechanical resistance, which can be modulated beforehand so as to be adaptable to various types of applications.

Another aim of the invention is to provide a cross-linkable modified collagen whose flexibility and cross-linking performances make it a raw material which is particularly appropriate for the elaboration, for example by molding or extrusion, of solid medical items of the implant or prosthesis type.

Consequently, it is after carrying out numerous trials and studies that the Applicant succeeded in overcoming the obstacles with which the prior art was faced and in achieving these aims and others by directly attaching cysteic residues to collagen with high grafting levels.

DISCLOSURE OF THE INVENTION AND BEST WAY OF IMPLEMENTING IT

Thus, the present invention relates to a new modified collagen which is soluble in water and/or in aprotic polar organic solvents and which contains free or substituted thiol functional groups carried by residues of cysteine or its derivatives, said residues being, at least partially, residues which are directly attached to collagen, characterized in that it possesses a level of thiol functional groups greater than 0.3, preferably 0.5 millimoles (mM/g) of collagen.

The residues of cysteine or its derivatives (designated hereinafter, without distinction, under the general term: "cysteic" residues), are directly linked to collagen via their carboxylic functional group(s) and correspond to the following general formula:

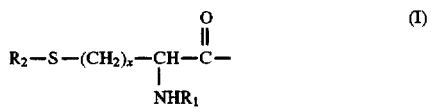
(I)

in which:

x is an integer, preferably equal to 1 or 2, which corresponds to the cysteine and homocysteine skeleton respectively, $R_1$ is hydrogen or a hydrocarbon radical, preferably chosen from acyl, alkyloxycarbonyl, aryloxycarbonyl or aralkyloxycarbonyl radicals;

$R_2$ is hydrogen or a hydrocarbon radical, preferably chosen from the following radicals: alkyloxycarbonyls, aryloxycarbonyls or aralkyloxycarbonyls, aralkyls, thioalkyls, thioaryls or thioaralkyls.

In accordance with a preferred embodiment of the invention, the modified collagen is cross-linkable.

For the purposes of the present invention, the term "cross-linkable" designates modified collagens which are capable of becoming self-cross-linked, spontaneously or by means of an intermediate step which is easy to carry out, such as oxidation.

Most advantageously, the cross-linkable modified collagen according to the invention is easy to shape and handle industrially. It makes it possible to obtain medical items of the implant, prosthesis or artificial skin type which are non-toxic, non-immunogenic and whose mechanical and biological properties are perfectly adapted to the intended application.

The level of substitution of this modified collagen which can be cross-linked via free thiol functional groups can vary within a wide range of values.

This is particularly advantageous with regard to adaptability, especially from the point of view of the mechanical properties, of the biomaterial to various final applications.

This modified collagen can be combined with other polymeric materials which can be used in the elaboration of biomaterials.

In this preferred embodiment, the substituent $R_2$ of the general formula of the cysteic residue is removable, so as to regenerate an SH ($R_2$=H), giving access to the cross-linking ability. $R_2$ preferably corresponds to the following substituents:

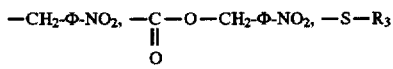

with $R_3$=Φ or:

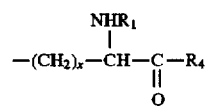

$R_4$ being equal to OH, NH—coll, O—coll.

As above, x is preferably equal to 1 or 2 (cysteine/homocysteine), and $R_1$ may consist of the radicals given hereinbefore. There may be mentioned in particular:

Hydrogen, 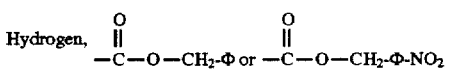

In the above formulae and in the remainder of the present account, the phenyl radical is designated by the symbol Φ and a collagenic chain by the abbreviation coll.

According to an advantageous variant of the invention, the substituent $R_1$ is a polymeric unit of the following formula:

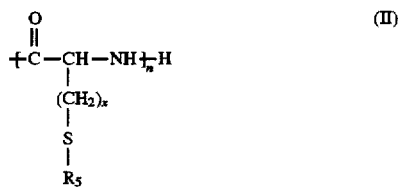
(II)

in which:
x is as defined above,
$n \geq 2$,
$R_5$=H, —S—Φ or:

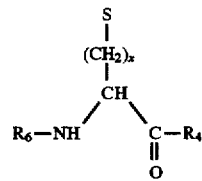

with $R_6$=H or the polymeric unit (II) defined above and with $R_4$=OH, NH—coll, O—coll. When $R_4$=NH—coll and/or O—coll, the collagen is in its cross-linked form.

The present invention also comprises non-cross-linkable modified collagens. Such is especially the case when, in the general formula of the cysteic residues given above, the radical $R_2$ corresponds to one of the following substituents:

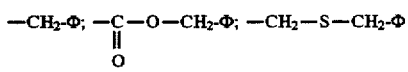

The direct grafting of the cysteic residues onto the nucleophilic functional groups (OH, $NH_2$) of the amino acids of the collagen provide access to substitution levels greater than those obtained up until now. It results in improved mechanical properties for the cross-linked product obtained from the (cross-linkable) modified collagen.

The passage of this modified collagen to the cross-linked state can be easily carried out by oxidation of the thiol functional groups and creation of disulfide bridges in a mild oxidizing environment. Under physiological conditions in vivo, this may occur via auto-oxidation by dissolved oxygen or via enzymatic oxidation, whereas under nonphysiological conditions in vitro, the oxidation can take place by means of non-toxic reagents such as hydrogen peroxide, atmospheric oxygen or iodine.

The cross-linked polymer can be obtained in a form which is very stable and possessing a high mechanical resistance.

The invention also relates, as new product, to a cross-linked collagen which is insoluble especially in water and/or in organic solvents, characterized in that its interchain bridges essentially consist of disulfide bridges formed by cysteic residues which are, at least partially, cysteic residues directly grafted onto the collagen in a level greater than 0.3, preferably 0.5 mM of free or substituted thiol functional groups per g of collagen.

This cross-linked collagen can be obtained from the self-cross-linkable modified collagen described above.

Furthermore, the present invention relates to a process for the production of a modified collagen which is soluble in water and/or in aprotic polar organic solvents and comprising free or substituted thiol functional groups carried by residues of cysteine or its derivatives, these cysteic residues being, at least partially, residues which are directly grafted onto the collagen.

This process constitutes a possibility, among others, of obtaining the collagens according to the invention described hereinbefore.

In accordance with a preferred embodiment, the process consists essentially in:

placing the starting collagen in a solvent, in a homogeneous or dispersive medium, protecting the free thiol and amine functional groups of the cysteic residue used, activating the acid functional group(s) of the said residue.

The novelty of this process lies in the use of an anhydrous solvent or dispersive medium for the starting collagen, and in that the protected and activated residues are reacted with the starting collagen, in the presence of an organic base and in the absence of water so as to obtain the desired modified collagen.

The merit of the Applicant is to have shown that these operating characteristics form part of those which are essential in order to achieve high levels of grafting of cysteic residues, and therefore of free or substituted thiol functional groups, onto the collagen.

In particular, it has been discovered that the reaction of the collagen with the cysteic residue suitably protected and activated by formation of anhydride or ester, in the presence of an organic base and in the absence of water, is one of the determining elements for the optimization of the grafting.

The starting material used in this process may be animal or human collagen having telopeptides or not.

According to the selected method of activation of the acid functional group(s), it may be advantageous either to solubilize the starting collagen in an anhydrous organic solvent such as dimethyl sulfoxide (DMSO), dimethylacetamide (DMAC), N-methylpyrrolidone (NMP), or to disperse it in an anhydrous organic medium such as tetrahydrofuran (THF).

In the case where solubilization is used, it is preferably carried out by means of a solubilization aid which may be a solvent such as for example methanol or a carboxylic acid.

Advantageously, the organic base is a tertiary amine.

According to a particularly advantageous arrangement of this first embodiment of the process of the invention, the modified collagen obtained is a precursor of a collagen which can be cross-linked essentially by formation of disulfide bridges from SH functional groups.

In this case, one of the possible means of protecting the thiol functional group of the cysteic residue used is to introduce this thiol functional group in a disulfide bridge. Thus, cysteine is preferably used as cysteic residue.

According to a variant protection of the thiol functional group, which leads to cross-linkable collagen, there is grafted onto this thiol functional group a hydrocarbon $R_2$ radical preferably selected from the following substituents:

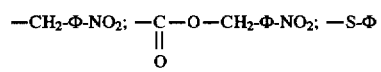

To obtain this cross-linking ability, it is necessary that $R_2$ is removable and convertible to SH, a radical which gives access to the "cross-linkability".

As regards the $NH_2$ functional groups, they are protected by the grafting of a $R_1$ group chosen from acyl, aryloxycarbonyl, alkyloxycarbonyl or aralkyloxycarbonyl radicals, the following radicals being particularly preferred:

The benzyloxycarbonyl groups are very widely used in peptide synthesis, in particular for protecting amines (see: "The carbobenzoxy and related groups—Chemistry of the amino acids", J. P. GREENSTEIN and M. WINITZ, 1961, 2, 887–901, published by J. WILEY, NEW YORK).

The optimization of the grafting of the cysteic residue onto the collagen also occurs via activation of the acid functional group(s) of this graft by formation of anhydrides or ester, for example.

Among the different techniques for activation by formation of anhydride, which are used in peptide synthesis, the Applicant selected three which are particularly suitable but not limiting for implementing the process in accordance with the invention.

The first among them consists in reacting each acid functional group of the cysteic residue with a reagent which makes it possible to obtain a mixed anhydride having high affinity towards the amine-containing and hydroxylated nucleophilic radicals of the collagen.

Another route for protecting thiol and amine The reactive agent used is a compound of formula:

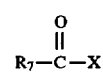

in which $R_7$ is an aliphatic and/or alicyclic and/or aromatic hydrocarbon radical, tert-butyl being preferred, and X is a halogen such as chlorine.

Pivaloyl (trimethylacetyl) chloride is particularly suitable as reactive agent:

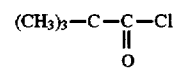

The second route for activation of the acid functional group(s) consists in forming mixed carbonic anhydrides by means of a compound of formula:

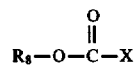

in which $R_8$ is an aliphatic and/or alicyclic and/or aromatic hydrocarbon radical, preferably of the alkyl, and still more preferably, ethyl type, and X is a halogen.

As an example, ethyl chloroformate can be mentioned:

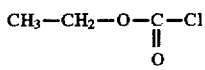

The anhydride formed is reactive towards the amines and hydroxyls of the collagen.

The third method of activation is a formation of N-carboxyanhydrides. It applies when the cysteic residue has one or more amine functional group(s) protected by N-acylalkoxylated, for example ethyloxy, methyloxy or benzyloxy, radicals. The activation is, in this case, achieved by conversion of the acid functional group(s) of the residue to acid halide, preferably acid chloride, which then reacts with the N-acylalkoxylated end(s) according to an intramolecular cyclization mechanism, resulting in LEUCH anhydrides.

In the case where the cysteic residue is cystine, the LEUCH anhydride formed has the following formula:

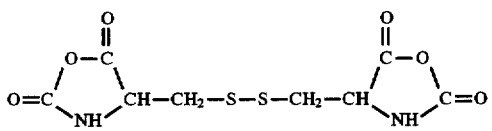

As regards the activation of the carboxylic acid functional group(s) by formation of ester, it is based on techniques known in peptide synthesis, see:

"the peptides: Analysis, Synthesis and Biology", GROSS E., Meienhofer, J. Eds. Academic Press. Inc. (London), 1979, "Principles of Peptide Synthesis", BODANSKY M., Springer-Verlaz (Berlin), 1984.

It is thus carried out by means of an aliphatic and/or aromatic and/or alicyclic and/or non-aromatic heterocyclic alcohol.

As examples of appropriate alcohols, there may be mentioned N-hydroxybenzotriazole, N-hydroxy-succinimide or p-nitrophenol and the like.

In accordance with the process according to the invention, the step, which follows the protection of the thiol and amine functional groups and the activation of the acid functional groups of the cysteic residue, is that where the latter is reacted with the starting collagen, optionally in the presence of an organic base and, preferably, in the absence of water, so as to obtain either the desired modified collagen or a precursor of the desired modified cross-linkable collagen.

The general conditions of this reaction are deduced from rules which are defined in peptide synthesis and which depend on the type of protection and activation used.

More specifically and in accordance with one of the essential characteristics of the process according to the invention, this reaction should be carried out in the presence of an amine-containing base of the tertiary type, preferably triethylamine.

This base increases the nucleophilicity and therefore the reactivity of the free amines of the lysyl residues of collagen.

It is advantageously in a quantity sufficient to neutralize the carboxylic functional groups of the acid residues of collagen (aspartic and glutamic acids representing about 9% on a numerical basis of the amino acids of collagen), as well as the acidic products optionally formed during the grafting.

When the cysteic residues have undergone an "anhydride" activation of their acid functional groups according to the first or second method of activation described above, they are reacted with collagen solubilized in an organic and anhydrous homogeneous solvent medium.

In contrast, provided that they are activated according to the third method of "anhydride" activation, the collagen used is in suspension in a dispersive and heterogeneous anhydrous medium of the aprotic organic solvent type.

The temperatures and reaction times are a function of the type of cysteic residues used (1st and 2nd embodiment) and/or of the type of activation (anhydride, ester and the like) of said residues. The adjustment of these parameters is an operation which is within the capability of a person skilled in the art for the field considered.

After reacting, the products are precipitated either by means of an organic solvent such as ethyl acetate, acetone or ethyl ether, when a solution is used, or filtered when the reaction medium is dispersive and heterogeneous.

There is thus finally obtained either a modified collagen or a precursor of collagen SH, it being possible for this precursor to be collagen linked to a cystine when the latter is chosen as cysteic residue, or collagen linked to a cysteic residue whose sulfur-containing end is linked to a protecting radical, for example of the type:

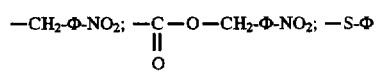

Within the framework of the third method of "anhydride" activation, the cysteic residue, comprising N-carboxyanhydrides, can bring about the formation of a modified collagen upon which are grafted polycysteic residues of formula:

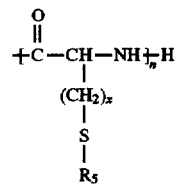

Such a modified collagen can itself also be a precursor of collagen SH.

The conversion of the cross-linkable collagen precursor is obtained by reduction by means of specific reducing agents or by catalytic hydrogenation, according to the protecting group used: the protecting groups linked via a disulfide bridge are removed by reduction, the others by catalytic hydrogenation.

The specific reducing agents are, e.g. β-mercaptoethanol, mercaptoacetic acid, mercaptoethylamine, benzyl mercaptan, thiocresol or alternatively dithiothreitol.

They can also be formed by a salt such as for example sodium borohydride or sodium hydrogen sulfite. Phosphines such as tributylphosphine are also quite suitable as reducing agent.

In practice, β-mercaptoethanol or dithiothreitol are preferably used.

This conversion step makes it possible to resolubilize the collagens which are then dialyzed against distilled water and then freeze-dried. The final product obtained is a modified collagen containing more than 0.3 mM thiol functional groups carried by cysteic residues, per gram of collagen.

This modified collagen can be subjected to an oxidation which results in the formation of disulfide bridges between the collagenic chains. A three-dimensional network is thus obtained which is insoluble in physiological media and soluble in reducing media capable of reducing the disulfide bridges.

The level of cross-linking is critical with respect to the mechanical resistance and the biodegradability of the cross-linked products obtained.

The reagents used during the chemical modifications are either convertible to non-toxic products or easily removable by non-degradative processes such as dialysis for example.

The modified collagen in reduced form does not contain residual activated functional groups and the oxidized cross-linked collagen can contain only unreacted thiol functional groups. These functional groups are not toxic since they occur naturally in a large number of animal proteins.

The oxidation processes do not involve toxic substances or conditions which are aggressive for living tissues.

The invention offers the highly welcome possibility of being able to control the kinetics and the level of cross-linking of the collagen.

Another important advantage of the invention is that it makes it possible to modulate the mechanical properties by controlling the number of cysteic residues introduced per unit of collagen mass.

It should be underlined that the products according to the invention are sterilizable by conventional methods of sterilization of biological polymers.

It follows that the cross-linkable products according to the invention find immediate applications, on the one hand, in human medicine and, on the other hand, in the biological field.

In human medicine, these may be implants, for example ophthalmological implants, prostheses, for example bone prostheses, dressings in the form of films or felts, artificial tissues (epidermis, vessels, ligaments, bone), bioencapsulation systems (microspheres, microcapsules) which permit the controlled release of active principles in vivo, coatings for biocompatibilization of implantable medical items or even, in addition, suture threads.

In biology, the materials according to the invention constitute excellent supports for two-dimensional (films) and three-dimensional (felts) cell cultures.

The cross-linked collagen according to the invention can be used alone or mixed with modified or unmodified biological polymers or synthetic polymers.

For each of the abovementioned biomedical applications, it is essential to have available a cross-linked collagen possessing determined and specific physico-chemical, mechanical or biological properties. Consequently, it is necessary to perfectly control the chemical modifications of collagen so as to be able to produce a wide range of cross-linkable collagens and thus respond, satisfactorily, to most of the constraints which appear during the elaboration of the specifications for a given application. As evident from the above description, the invention perfectly meets this requirement.

Other advantages and variants of the present invention are clearly evident from the example of implementation of the process according to the invention given hereinbelow.

EXAMPLES

Example 1: Preparation of Modified, in Particular Thiolyzed, Collagens by Means of Cystine and by "Anhydride" Activation of the Acid Functional Groups A—Methodology 1—Preparation of the Collagen:

The collagen used in this example is the atelocollagen marketed by the company SADUC and consisting of a mixture of atelocollagen types I and III extracted from calf skin.

In the case where the activation of the acid functional groups is obtained by formation of mixed anhydrides or mixed carbonic anhydrides, the collagen is dissolved in a polar, aprotic and anhydrous organic medium. This consists, firstly, of causing it to swell in a solubilization aid consisting of methanol (15 ml/g of collagen to be dissolved). An organic solvent, namely DMAC, is then added, which makes it possible to solubilize the collagen, which remains in this state after evaporation of the methanol under reduced pressure. A concentrated solution, containing up to 8% collagen can thus be prepared.

When the activation of the carboxyl functional groups is carried out by formation of a LEUCH anhydride, the collagen is suspended in tetrahydrofuran.

2—Prior Treatment of the Cysteic Residue:

The cysteic residue used here is cystine. Ideal protection of the thiol functional group thus exists.

The masking of the amine functional groups of this cystine remains to be carried out.

For that, 15.3 g of benzyl chloroformate in suspension in 120 ml of 1N sodium hydroxide are added to 7.2 g of L-cystine dissolved in 60 ml of 1N sodium hydroxide. After stirring for three hours, the medium is acidified to pH2 by means of 6N HCl. The precipitate obtained is extracted with ethyl acetate. The organic phase, dried over anhydrous sodium sulfate is evaporated and the oily residue obtained is taken up in 400 ml of chloroform: N,N'-dibenzyloxycarbonylcystine then gradually crystallizes in the form of long needles. The acid functional groups of the cystine derivative are then activated using one of the following three techniques: a, b, c.

a) Activation by formation of mixed anhydrides:

Use of pivaloyl (trimethylacetyl) chloride:

The action of pivaloyl chloride on a carboxylic acid results in the formation of a mixed anhydride which is very reactive towards amines and alcohols. 790 µl (2 equivalents) of triethylamine are added to 1.44 g of N,N'-dibenzyloxycarbonylcystine, dissolved in 12 ml of THF.

After cooling the medium to −5° C., 698 µl (2 equivalents) of pivaloyl chloride are added. The reaction is continued for 2 hours at −5° C., then for 1 hour at room temperature. The triethylammonium hydrochloride precipitate is then filtered and the THF evaporated under reduced pressure. The oil obtained is used immediately after preparation as it is for the reaction.

b) Activation by formation of mixed carbonic anhydrides:

Use of ethyl chloroformate:

The action of ethyl chloroformate on a carboxylic acid results in the formation of a mixed carbonic anhydride which is very reactive towards amines and alcohols.

790 µl (2 equivalents) of triethylamine are added to 1.44 g of N,N'-dibenzyloxycarbonylcystine, dissolved in 12 ml of THF.

After cooling the medium to −10° C., 540 µl of ethyl chloroformate (2 equivalents) are added in three portions. The reaction is continued at this temperature for 30 minutes, then the triethylammonium hydrochloride formed is filtered and the THF evaporated under reduced pressure. The oil obtained is used immediately after preparation as it is for the reaction.

c) Activation by formation of LEUCH anhydride:

The heating of an N-acylalkoxylated (ethoxylated, methoxylated, benzomethoxylated and the like) amino acid, whose acid functional group is activated in the form of an acid halide, results in intramolecular cyclization, with formation of an N-carboxyanhydride, also called LEUCH anhydride. This type of compound is reactive towards amines and alcohols and should be protected from moisture. The formation of the LEUCH anhydride of cystine occurs in two stages, as indicated hereinbelow. 1.95 equivalent of PCl$_5$ is added to N,N'-dibenzyloxycarbonylcystine, in solution at 10% in dioxane. After stirring for 15 minutes with cooling, the reaction medium is placed at 40° C. The LEUCH anhydride of cystine then crystallizes gradually. The reaction is continued for one hour, then the crystals are filtered, rinsed with dioxane and dried under vacuum.

3—Reaction of the Protected and Activated Cysteic Residue with Collagen:

The procedure is identical for all the residues activated according to techniques a, b, c outlined above.

Triethylamine is added in sufficient quantity to the collagen dissolved in DMAC (techniques a), b)) or in suspension in THF (technique c)). After stirring for 15 minutes, the media are brought to the reaction temperature and the activated cystine derivatives are added. For each activated cystine residue, the exact reaction conditions are indicated in Table I below.

After reaction, the collagens (techniques a and b) are precipitated with ethyl acetate, washed with ethyl acetate, and then rinsed with acetone. For technique c, the collagen, dispersed in THF, is filtered and then rinsed with THF.

The modified collagens obtained are suspended in water (concentration 5% (p/v) for a and b, 1% (p/v) for c). 1 equivalent of dithiothreitol per mole of cystine derivative introduced into the reaction is added to the collagens and the pH is adjusted to 9.5 with sodium hydroxide. The reduction is continued for 18 hours at room temperature. It makes it possible to solubilize the collagens.

These collagens are then precipitated at pH=2 with hydrochloric acid, dialyzed under nitrogen at pH=3, and then freeze-dried.

TABLE I

CONDITIONS FOR REACTING THE ACTIVATED CYSTINE DERIVATIVES WITH COLLAGEN

| Samples | -I- Pivaloyl chloride | -II- Ethyl chloroformate | -III- LEUCH anhydride |
|---|---|---|---|
| Collagen | 1 g | 1 g | 1 g |
| Solvent | DMAC | DMAC | THF |
| Medium | homogeneous | homogeneous | heterogeneous |
| Collagen concentration | 5% (p/v) | 5% (p/v) | 5% (p/v) |
| Quantity of activated acid functional groups | 3 eq*/substitutable functional group | 3 eq*/substitutable functional group | 3 eq/substitutable functional group |
| Et$_3$N | 190 µl | 1.12 ml | 1.12 ml |
| Temperature | −5° C. then gradual return to RT | −10° C. then gradual return to RT | Cooling to −75° C. before addition of the anhydride, then −35° C. |
| Reaction time | 20 hours | 20 hours | 20 hours | eq: equivalent.
*: based on a cysteic residue activation yield of 100%
RT: Room temperature.
B - RESULTS Samples I, II, III of modified collagen are subjected to analysis of their cysteine content according to the SH assay technique using dithionitrobenzoic acid (DTNB) described in G. L. ELMANN, Arch. Biochem. Biophys, 1959, 82-70.

The addition of DTNB to a solution containing free SH groups results in the appearance of a yellow color which is proportional to the quantity of thiols present (33). A hydrolysis step in reducing medium is previously carried out. It permits the breaking of the disulfide bridges into SH groups which are the only ones to be assayed.

1 ml of 4N NaOH, containing 1% NaBH$_4$ is added to 20 mg of collagen (native or modified). After two hours of hydrolysis at 70° C., the media are acidified with 6N HCl until the evolution of gas ceases. The controls are then diluted 1/500 and the samples 1/200 with 0.1M acetate buffer, pH=5.

100 µl of a 10 mM DTNB solution, prepared in 0.1M phosphate buffer, pH=7.2, are added to 2 ml of these solutions. The absorption of the samples at 410 nm is measured after 10 minutes of incubation in the dark. The quantities of cysteine in the samples are calculated from the calibration series for cysteine (0–20 µg/ml).

The results are presented in Table 2 below.

TABLE 2

| Samples | mean concentration in SH (%) * |
|---|---|
| Native collagen | 0 |
| I | 0.64 ± 0.05 |
| II | 0.41 ± 0.02 |
| III | 1.59 ± 0.46 |

* = mM of SH functional groups/g of collagen.

This Table shows that the process according to the invention makes it possible to obtain modified collagens which are cross-linkable and containing at least three cysteic residues per 100 amino acids of collagen.

We claim:

1. A modified collagen which is soluble in a solvent selected from the group consisting of water, aprotic polar organic solvents and mixtures thereof and which comprises free or substituted thiol functional groups carried, by residues of cysteine or its derivatives, wherein at least a portion of said residues is grafted directly onto collagenic chain, wherein said modified collagen possesses a level of free or substituted thiol functional groups greater than 0.3 mM/gram of collagen.

2. The modified collagen of claim 1 wherein said modified collagen possesses a level of free or substituted thiol functional groups greater than 0.5 mM/gram of collagen.

3. The modified collagen according to claim 1 wherein the cysteic residues have the following general formula:

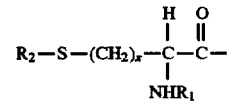

in which:

x is an integer having a value so that said formula includes the skeleton of cystein, homocystein or a homologue thereof, R$_1$ is hydrogen or a hydrocarbon radical, R$_2$ is hydrogen or a hydrocarbon radical.

4. The modified collagen according to claim 3, wherein R$_2$ is selected from the group consisting of

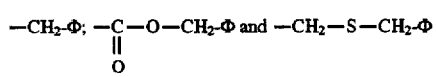

5. The modified collagen according to claim 3 wherein R$_1$ is selected from the group consisting of

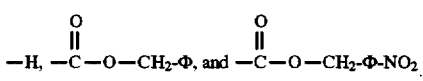

6. The modified collagen according to claim 3, wherein $R_1$ is a polymer unit of the following formula:

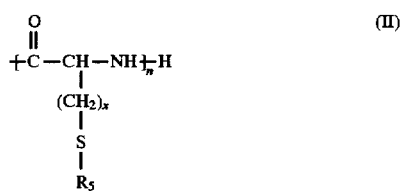

in which:

$n \geq 2$, $R_5 = H$, —S—Φ or:

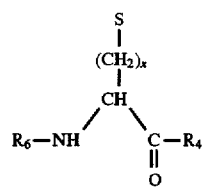

with $R_6 = H$ or the polymer unit (II) defined above and with $R_4 = OH$, NH—coll, or O—coll.

7. The modified collagen of claim 3 wherein $R_1$ is selected from the group consisting of acyl, alkyloxycarbonyl, aryloxycarbonyl and aralkyloxycarbonyl and $R_2$ is selected from the group consisting of alkyloxycarbonyl, aryloxycarbonyl, aralkyloxycarbonyl, aralkyl, thioalkyl, thioaryl, and thioaralkyl.

8. The modified collagen according to claim 3, wherein said modified collagen is cross-linkable.

9. The collagen of claim 8 wherein $R_2$ is selected from the group consisting of

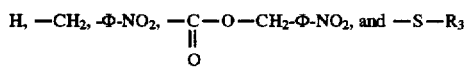

wherein $R_3$ is selected from the group consisting of Φ and

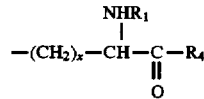

and wherein $R_4$ is selected from the group consisting of:

OH, NH—coll, and O—coll.

10. An insoluble cross-linked collagen, wherein its interchain bridges essentially consist of disulfide bridges formed by cysteic residues wherein at least a portion of said cysteic residues is directly grafted onto the collagen in a level greater than 0.03 mM of free or substituted thiol functional groups per gram of collagen.

11. The insoluble cross-linked collagen of claim 10 wherein said cysteic residues are directly grafted onto the collagen on a level greater than 0.5 mM of free or substituted thiol functional groups per gram of collagen.

12. A process for the production of a modified collagen which is soluble in a solvent selected from the group consisting of water, aprotic polar organic solvents, and mixtures thereof and comprising free or substituted thiol functional groups carried by residues of cysteine or its derivatives, wherein at least a portion of said residues is directly grafted onto the collagen, said process comprising of placing a starting collagen in a solvent or dispersive medium, protecting the free thiol and amine functional groups of the cysteic residue used, activating the acid functional group(s) of the said residues, wherein the solvent or dispersive medium for the starting collagen is anhydrous and in that the protected and activated residues are reacted with the starting collagen, in the presence of an organic base, and in the absence of water so as to obtain the desired modified collagen.

13. The process according to claim 12 wherein the protection of the free or substituted thiol functional groups is obtained by selecting cystine as cysteic residue and in that the amine functional groups are protected by grafting of a $R_1$ group selected from the group consisting of acyl radicals.

14. The process of claim 13 wherein said acyl radicals are selected from the group consisting of

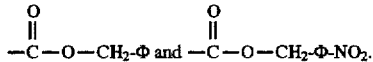

15. The process according to claim 12, wherein the protection of the free thiol and amine functional groups of the cysteic residue is carried out by formation of thiazoline.

16. The process of claim 15 wherein the protection of the free thiol and amine functional groups of the cysteic residue is carried out by formation of an alkylated thiazolidine.

17. The process according to claim 12, wherein the activation of the acid functional group(s) is carried out by formation of a mixed acid anhydride, by means of a compound of formula:

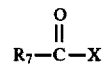

in which $R_7$ is selected from the group consisting of aliphatic hydrocarbon radical, alicyclic hydrocarbon radical, aromatic hydrocarbon radical and mixtures thereof, and X is a halogen.

18. The process of claim 17 wherein $R_7$ is tert-butyl.

19. The process according to claim 12, wherein the cysteic residue is N-acylalkoxylated and in that the activation of the acid functional group(s) is carried out by formation of an N-carboxyanhydride, by means of an acid halide which reacts with the N-acylalkoxylated end(s) to give an N-carboxyanhydride by intramolecular cyclization.

20. The process of claim 19 wherein said acid halide is acid chloride.

21. The process according to claim 12, wherein the activation of the acid functional group(s) is carried out by formation of an ester by means of an alcohol selected from the group consisting of an aliphatic alcohol, aromatic alcohol, alicyclic alcohol, non-aromatic heterocyclic alcohol and mixtures thereof.

22. The process of claim 21 wherein said non-aromatic heterocyclic alcohol is N-hydroxybenzotriazole.

23. The process of claim 12 wherein said organic base is an amine.

24. The process of claim 23 wherein said amine is a tertiary amine.

25. The process according to claimed 12, wherein the activation of the acid functional group(s) is carried out by formation of a mixed acid carbonic anhydride, by means of a compound of formula:

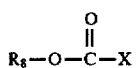

in which $R_8$ is selected from the group consisting of aliphatic hydrocarbon radical, alicyclic hydrocarbon radical, aromatic hydrocarbon radical, and mixtures thereof, and X is a halogen.

26. The process of claim 25 wherein $R_8$ is an alkyl radical.

27. The process of claim 26 wherein said alkyl is ethyl.

28. The process according to claim 12, wherein the modified collagen obtained is a precursor of a collagen which can be cross-linked essentially by formation of disulfide bridges from SH functional groups.

29. The process according to claim 28, wherein the precursor is converted to collagen S—H by reduction by means of specific reducing agents or by catalytic hydrogenation or by acid hydrolysis.

30. The process of claim 29 wherein said reducing agents are selected from the group consisting of β-mercaptoethanol and dithiothreitol.

* * * * *